United States Patent [19]

Tohyama et al.

[11] 4,177,109
[45] Dec. 4, 1979

[54] γ-GLUTAMYL-P-AMINOANILIDE DERIVATIVES FOR MEASURING ACTIVITY OF γ-GLUTAMYL TRANSPEPTIDASE

[75] Inventors: Takanori Tohyama; Masaaki Nakahata, both of Kawagoe, Japan

[73] Assignee: Wako Pure Chemical Industries, Ltd., Osaka, Japan

[21] Appl. No.: 910,830

[22] Filed: May 30, 1978

[30] Foreign Application Priority Data

May 30, 1977 [JP] Japan .................................. 52/63061

[51] Int. Cl.² ............................................. G01N 33/14
[52] U.S. Cl. ................................. 435/24; 260/507 R;
562/450
[58] Field of Search .................................. 195/103.5 R

[56] References Cited
U.S. PATENT DOCUMENTS 3,892,631  7/1975  Carroll .......................... 195/103.5 R
3,986,931  10/1976  Bernt et al. .................... 195/103.5 R
4,087,331  5/1978  Bucolo et al. ............. 195/103.5 R X

OTHER PUBLICATIONS

Rosalki et al, Clinical Chemistry, vol. 20, No. 9, pp. 1121–1124, (1974).

Primary Examiner—Lionel M. Shapiro
Attorney, Agent, or Firm—Armstrong, Nikaido, Marmelstein & Kubovcik

[57] ABSTRACT

A γ-glutamyl-p-aminoanilide derivative of the formula:

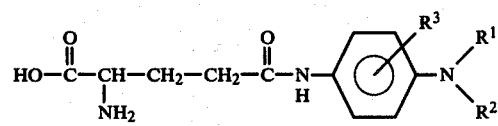

wherein $R^1$ and $R^2$ are independently lower alkyl; and $R^3$ is hydrogen, lower alkyl, carboxyl or sulfo, can be produced by reacting a N-phthalyl-γ-glutamyl-p-aminoanilide derivative with hydrazine. The γ-glutamyl-p-aminoanilide derivative can be used as a substrate for measuring γ-glutamyl transpeptidase activity in a living sample.

7 Claims, No Drawings

γ-GLUTAMYL-P-AMINOANILIDE DERIVATIVES FOR MEASURING ACTIVITY OF γ-GLUTAMYL TRANSPEPTIDASE

This invention relates to γ-glutamyl-p-aminoanilide derivatives, a process for producing the same and a method for measuring γ-glutamyl transpeptidase activity in a living sample by using the same.

γ-Glutamyl transpeptidase (hereinafter referred to as "γ-GTP") is an enzyme which relates to metabolism of γ-glutamyl peptide in a living organism and transfer the γ-glutamyl group in γ-glutamyl peptide to other peptides or amino acids and the like. Measurement of γ-GTP activity in blood is a useful testing method for diagnosis or grasp of the condition of such a disease as active type chronic heptatitis, bilis stagnant heptatitis, obstructive jaundice, primary or metastatic cancer of the liver, or the like.

As a substrate for measuring γ-GTP activity, there have been known γ-glutamyl-p-nitroanilide, γ-glutamyl-α-naphthylamide, γ-glutamyl-β-naphthylamide. But when these compounds are used as substrate, there are many defects in that blank tests of specimens should be carried out under severe conditions, severe conditions for the measurement should be applied, complicated and elaborate operations are necessary, there is no suitable color producing reagent having good color stability, α-naphthylamine and β-naphthylamine which are used as standard substance are carcinogenic compounds, and the like.

It is an object of this invention to provide a γ-glutamyl-p-aminoanilide derivative which shows excellent properties as a substrate for measuring γ-GTP activity in a living sample. It is another object of this invention to provide a process for producing such a γ-glutamyl-p-aminoanilide derivative. It is a further object of this invention to provide a method for measuring γ-GTP activity in a living sample by using such a γ-glutamyl-p-aminoanilide derivative as a substrate. Further objects and advantages of this invention will be apparent to one skilled in the art from the accompanying disclosure and discussion.

This invention provides a γ-glutamyl-p-aminoanilide derivative of the formula:

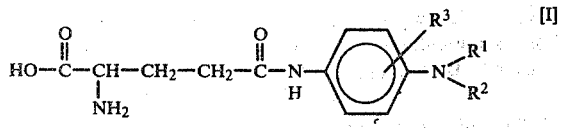

wherein $R^1$ and $R^2$ are independently a lower alkyl group, and $R^3$ is hydrogen, a lower alkyl group, a carboxyl group or a sulfo group.

This invention also provides a process for producing the γ-glutamyl-p-aminoanilide derivative of the formula (I) by reacting a N-phthalyl-γ-glutamyl-p-aminoanilide derivative of the formula:

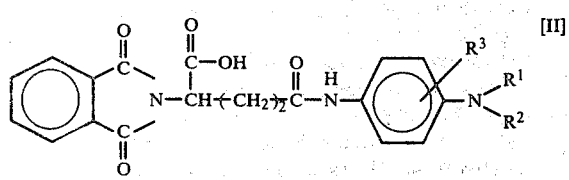

wherein $R^1$, $R^2$ and $R^3$ are as defined above, with hydrazine preferably in a solvent at a temperature of preferably from 0° C. to 60° C.

In the above formulae, the lower alkyl group means that having 1 to 5 carbon atoms such as methyl, ethyl, propyl, isopropyl, butyl, isobutyl, amyl and the like.

Examples of N-phthalyl-γ-glutamyl-p-aminoanilide derivatives of the formula (II) are N-phthalyl-γ-glutamyl-p-(N,N-dimethylamino)anilide, N-phthalyl-γ-glutamyl-p-(N,N-diethylamino)anilide, N-phthalyl-γ-glutamyl-p-(N,N-dipropylamino)anilide, N-phthalyl-γ-glutamyl-o-methyl-p-(N,N-dimethylamino)anilide, N-phthalyl-γ-glutamyl-o-methyl-p-(N,N-diethylamino)anilide, N-phthalyl-γ-glutamyl-m-methyl-p-(N,N-diethylamino)anilide, N-phthalyl-γ-glutamyl-o-sulfo-p-(N,N-dimethylamino)anilide, N-phthalyl-γ-glutamyl-m-sulfo-p-(N,N-diethylamino)anilide, N-phthalyl-γ-glutamyl-m-carboxy-p-(N,N-dimethylamino)anilide, N-phthalyl-γ-glutamyl-o-carboxy-p-(N,N-diethylamino)anilide, and the like.

Examples of γ-glutamyl-p-aminoanilide derivatives of the formula (I) are γ-glutamyl-p-(N,N-dimethylamino)anilide, γ-glutamyl-p-(N,N-diethylamino)anilide, γ-glutamyl-p-(N,N-dipropylamino)anilide, γ-glutayl-o-methyl-p-(N,N-dimethylamino)anilide, γ-glutamyl-o-methyl-p-(N,N-diethylamino)anilide, γ-glutamyl-m-methyl-p-(N,N-diethylamino)anilide, γ-glutamyl-o-sulfo-p-(N,N-dimethylamino)anilide, γ-glutamyl-m-sulfo-p-(N,N-diethylamino)anilide, γ-glutamyl-m-carboxy-p-(N,N-dimethylamino)anilide, γ-glutamyl-o-carboxy-p-(N,N-diethylamino)anilide, and the like.

The N-phthalyl-γ-glutamyl-p-aminoanilide derivative of the formula (II) can be prepared, for example, by reacting N-phthalylglutamic acid anhydride with a p-phenylenediamine derivative of the formula:

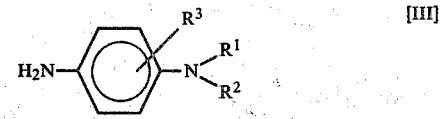

wherein $R^1$, $R^2$ and $R^3$ are as defined above, as follows:

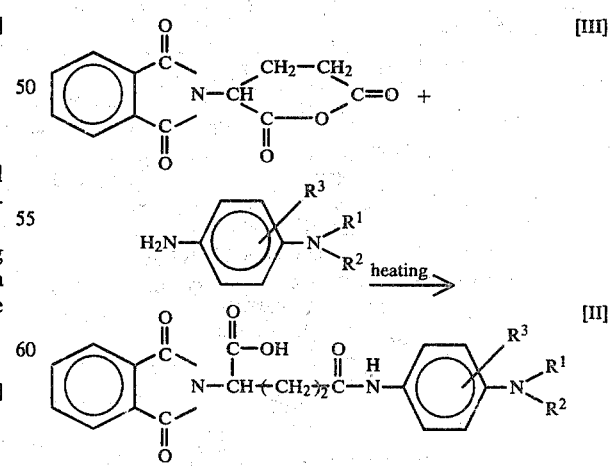

The reaction can be carried out by using a theoretical amount or a little excess of N-phthalylglutamic acid anhydride preferably in the presence of an organic solvent such as chloroform, and the like, if necessary in the presence of an organic acid such as acetic acid, and the like, at a temperature of from 20° C. to 100° C. After the reaction, the resulting N-phthalyl-γ-glutamyl-p-aminoanilide derivative of the formula (II) can be separated by a conventional method.

Examples of p-phenylenediamine derivatives of the formula (III) are N,N-dimethyl-p-phenylenediamine, N,N-diethyl-p-phenylenediamine, N,N-dipropyl-p-phenylenediamine, o-methyl-p-(N,N-dimethylamino)aniline, o-methyl-p-(N,N-diethylamino)aniline, m-methyl-p-(N,N-diethylamino)aniline, o-sulfo-p-(N,N-dimethylamino)aniline, m-sulfo-p-(N,N-diethylamino)aniline, m-carboxy-p-(N,N-dimethylamino)aniline, o-carboxy-p-(N,N-diethylamino)aniline, and the like.

The reaction of the N-phthalyl-γ-glutamyl-p-aminoanilide derivative of the formula (II) with hydrazine can be carried out as follows:

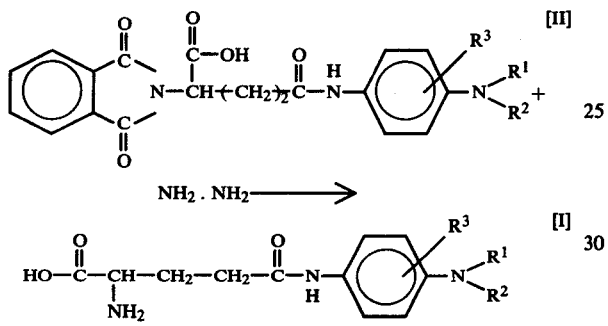

As the hydrazine, there can be used hydrazine itself (NH$_2$NH$_2$), hydrate of hydrazine (NH$_2$NH$_2$.H$_2$O), salts of these hydrazines such as mineral acid salts, e.g. sulfate, hydrochloride, and the like. Usually, hydrate of hydrazine (NH$_2$NH$_2$.H$_2$O) is used.

The use of a solvent in the reaction is preferable. Usually, water or an organic solvent which does not influence the reaction unfavorably can be used. Preferable examples of the organic solvents are water soluble polar organic solvents such as alcohols, e.g. methanol, ethaol, propanol, isopropanol, ethylene glycol, and the like; hydroxy ethers, e.g. methyl Cellosolve, ethyl Cellosolve, and the like; ether, e.g. tetrahydrofuran, dioxane, and the like.

The reaction is generally carried out at a temperature of from 0° C. to 60° C., preferably from 10° C. to 30° C. A theoretical amount or a little excess of hydrazine is used.

After the reaction, the end product of the formula (I) is separated, and if necessary purified, by using a conventional method.

The γ-glutamyl-p-aminoanilide derivative of the formula (I) has the same or more substrate affinity (substrate reactivity) to γ-GTP as γ-glutamyl-p-nitroanilide which has been used widely as a substrate for measuring γ-GTP activity as shown in the following Table.

Table

| | Substrate reactivity | |
|---|---|---|
| Substrate | Reacted amount (mIU) | Ratio |
| L-γ-Glutamyl-p-nitroanilide (Comparison) | 220[1] | 100.0 |
| L-γ-Glutamyl-p-(N,N-dimethylamino)-anilide | 230[2] | 104.5 |
| L-γ-Glutamyl-p-(N,N-diethylamino)-anilide | 223[2] | 101.4 |
| L-γ-Glutamyl-p-(N,N-dipropylamino)-anilide | 212[2] | 96.4 |
| L-γ-Glutamyl-o-methyl-p-(N,N-diethylamino)anilide | 194[2] | 88.2 |

Note:
[1]The value is measured according to a conventional method.
[2]The value is obtained according to the procedure described in Example 3 explained hereinafter.

Therefore, the γ-glutamyl-p-aminoanilide derivative of the formula (I) can sufficiently be used as a substrate for measuring γ-GTP activity.

This invention further provides a method for measuring γ-GTP activity in a living sample by using the γ-glutamyl-p-aminoanilide derivative of the formula (I) as a substrate.

According to a conventional method for measuring γ-GTP activity in a living sample using γ-glutamyl-p-nitroanilide as a substrate, the amount of p-nitroaniline liberated by γ-GTP can be obtained by measuring optical absorbance at 410 nm (= mμ), or alternatively γ-GTP activity can be calculated from optical absorbance at a maximum wavelength after color developing p-nitroaniline by using as a color producing reagent an aldehyde such as p-dimethylaminocinnamaldehyde, p-dimethylaminobenzaldehyde, or the like. But in the method of measuring absorbance of p-nitroaniline at 410 nm, since wavelengths of other components in the living sample are very close to the measuring wavelength, blank tests of the specimens should be carried out under severe conditions and remarkably severe conditions should be applied in order to obtain accurate data, which makes the procedure very complicated and elaborate. On the other hand, the method of color developing p-nitroaniline with an aldehyde such as p-dimethylaminocinnamaldehyde requires a severe, complicated and elaborate procedure in order to maintain accurate measurement by using a constant temperature cell, since optical absorbance of the color substance decreases with a decrease in temperature, for example, a value of absorbance at 37° decreases to a half of the value at 20° C. Consequently, the use of γ-glutamyl-p-nitroaniline as a substrate is not practical and is unsuitable as a daily testing method which requires accuracy and rapidity.

On the contrary, according to the method of this invention using the γ-glutamyl-p-aminoanilide derivative of the formula (I) as a substrate, γ-GTP activity in a living sample can be measured accurately and rapidly due to high sensitivity to coloration and rapid color developing reaction.

On measuring γ-GTP activity using the γ-glutamyl-p-aminoanilide derivative of the formula (I) as a substrate, the amount of p-phenylenediamine derivative produced by enzymatic γ-GTP activity is determined. On determining the amount p-phenylenediamine derivative, there can be applied various conventional methods for determining aromatic amines by color development such as a diazo coupling method, a method for determining Schiff base produced by reacting an aldehyde series compound, and the like, but the most preferable method is to determine the colored compound produced by oxidation from the viewpoint of rapidity of the operation and accuracy of the ata obtained. For example, a p-phenylenediamine derivative is oxidized preferably in the presence of a coupler capable of producing a coloring matter by oxidative condensation with the p-phenylenediamine derivative to produce a colored compound which is determined colorimetrically in order to measure γ-GTP activity.

Preferable pH on measuring γ-GTP activity using the γ-glutamyl-p-aminoanilide derivative of the formula (I) as a substrate is in the range of about 7.5 to 9.0. In order to maintain the pH in a suitable range, there may be used buffers such as phosphates, borates, carbonates, tris(hydroxymethyl)aminomethane, barbital, triethanolamine, glycine, and the like. Among them, inorganic salts such as borates, phosphates and carbonates are preferable.

The p-phenylenediamine derivative produced can easily be changed to a colored compound by the action of an oxidizer. In this case, oxidative condensation in the presence of a coupler is preferable. For example, if the oxidation is carried out at a pH of about 4 to 9, a compound having a maximum absorption at about 510 nm is obtained. If the oxidative condensation is carried out in the presence of a coupler such as a phenol, a naphthol, or the like, a colored compound having a maximum absorption at about 670 nm can be obtained. As couplers, any ones which form a coloring matter by oxidative condensation with the p-phenylenediamine derivative can be used. Examples of the couplers are phenol, α-naphthol, β-naphthol, and their derivatives such as monosulfonic acid derivatives, e.g. 1-naphthol-2-sulfonic acid, 1-naphthol-8-sulfonic acid, 2-naphthol-7-sulfonic acid, 2-naphthol-8-sulfonic acid, and the like and their salts, disulfonic acid derivatives, e.g. 2-naphthol-3,6-disulfonic acid, 2-naphthol-6,8-disulfonic acid, and the like and their salts, carboxylic acid derivatives, e.g. 1-naphthol-2-carboxylic acid, salicylic acid, and the like and their salts, polyhydric phenols, e.g. catechol, pyrocatechol, and the like.

The color developing reaction in the production of a colored compound by the oxidation or by the oxidative condensation in the presence of a coupler can be completed quantitatively at once at a pH of from about 4 to 12. In order to maintain the pH in the above-mentioned range, a buffer or an alkali such as alkali hydroxides, carbonates, phosphates, borates and the like can be used effectively.

Any oxidizers which can color develop the p-phenylenediamine derivative by oxidation or oxidative condensation can be used. Examples of the oxidizers are halogen series oxidizers such as periodates, chloroamine T, hypochlorites, and the like, peroxide series oxidizers such as persulfates and the like.

The colored compound produced by oxidative condensation of the p-phenylenediamine derivatives with the coupler is blue having a maximum absorption at about 670 nm which is hardly influenced by impurities showing absorptions at about 400 to 570 nm present in a living sample, sensitivity to coloration is very high, color stability is good, and absorbance hardly changes depending on temperature changes, so that the method for measuring γ-GTP activity in a living sample according to this invention is very accurate and practically useful.

The activity measuring method of this invention will be explained in more detail hereinafter. For example, to 1.0 ml of a buffer solution of 0.05 mole/1. of boric acid a pH 8.0 containing 10 mmole/1. or γ-glutamyl-p-(N,N-diethylamino)anilide and 20 mmole/1. of glycylglycine, a living sample, for exaple, 0.02 ml of serum is added and heated in a constant temperature bath at 37° C. for 15 minutes. The reaction solution is mixed with 1.0 ml of a 0.2% by weight phenol solution together with 1.0 ml of a 0.3 mole/1. boric acid buffer solution of pH 8.0 containing 0.2% by weight of potassium periodate. The reaction solution immediately shows a blue color having a maximum absorption at 670 nm. Optical absorbance of the reaction solution at 670 nm is measured and compared with a blank test sample obtained by using water in place of the serum sample. γ-GTP activity in the sample can be calculated by using a calibration curve prepared by a conventional method using known amounts of standard serum or N,N-diethyl-p-phenylenediamine.

If the substrate according to this invention is left to stand in the form of an aqueous solution, a p-phenylenediamine derivative may be liberated by hydrolysis. But this can be prevented by adding a buffer to the solution or by controlling the molar concentration of the buffer. For example, in the case of a phosphoric acid buffer solution of pH 8.0 or a tris buffer solution of pH 8.0, the lower the molar concentration of the buffer becomes, the less the liberation of p-phenylenediamine derivative becomes. On the other hand, in the case of borates, liberation of p-phenylenediamine derivative hardly takes place irrespective of their molar concentration.

Addition of an alcohol such as methanol, ethanol, propanol, butanol, ethylene glycol, propylene glycol, diethylene glycol, glycerin, or the like in the range of about 0.01 to 3.0% by weight based on the final weight of the colored solution to the solution to be measured gives good influence on color stability.

As mentioned above, if the γ-glutamyl-p-aminoanilide derivative of the formula (I) is used as a substrate in the measurement of γ-GTP activity in a living sample, γ-GTP activity can be measured accurately and rapidly without causing any problems in safety and sanitation for labor. Further, since sensitivity to coloration is high and the color developing reaction can be completed instantly, the measuring method of this invention can easily be applied to an automatic analyzing device.

This invention will be explained by way of the following examples, in which percents are by weight unless otherwise specified.

REFERENTIAL EXAMPLE 1

A mixture of 110 g of N-phthalyl-L-glutamic acid anhydride, 69.3 g of N,N-diethyl-p-phenylenediamine, 440 ml of chloroform, and 82.5 ml of acetic acid is refluxed for 1 hour with heating. After removing the chloroform by distillation, ethanol is added to form crystals. The crystals are filtered, washed and dried to give 160 g of N-phthalyl-L-γ-glutamyl-p-(N,N-diethylamino)ailide having a melting point of 189° C.–190.5° C.

Similarly, by using N,N-dimethyl-p-phenylenediamine, N,N-dipropyl-p-phenylenediamine, or o-methyl-p-(N,N-diethylamino)aniline in place of N,N-diethyl-p-phenylenediamine, there is obtained N-phthalyl-L-γ-glutamyl-p-(N,N-dimethylamino)anilide, N-phthalyl-L-γ-glutamyl-p-(N,N-dipropylamino)anilide or N-phthalyl-L-γ-glutamyl-o-methyl-p-(N,N-diethylamino)anilide, respectively.

EXAMPLE 1

To 10 g of N-phthalyl-L-γ-glutamyl-p-(N,N-diethylamino)anilide obtained in Referential Example 1, 70 ml of methanol and 13.2 ml of a 80% hydrazine hydrate aqueous solution are added and mixed. The resulting mixture is stirred at room temperature for 2 days to carry out the reaction. Subsequently, the reaction mixture is filtered, washed and dried to give 14.7 g of white crystals of L-γ-glutamyl-p-(N,N-diethylamino)anilide having a melting point pf 217°-220° C. (decomposition).

Elementary analysis:

|  | C (%) | H (%) | N (%) |
|---|---|---|---|
| Calcd. for $C_{15}H_{23}O_3N_3 \cdot 2HCl \cdot H_2O$ | 46.88 | 7.08 | 10.94 |
| Found | 47.27 | 7.27 | 10.78 |

$[\alpha]_D^{20} = +17.3°$ ($c=3.0$ in methanol)

EXAMPLE 2

Using N-phthalyl-L-γ-glutamyl-p-(N,N-dimethylamino)anilide obtained in Referential Example 1 in place of N-phthalyl-L-γ-glutamyl-p-(N,N-diethylamino)anilide used in Exaple 1, there is obtained L-γ-glutamyl-p-(N,N-dimethylamino)anilide in the same manner as described in Example 1. Similarly, using N-phthalyl-L-γ-glutamyl-p-(N,N-dipropylamino)anilide or N-phthalyl-L-γ-glutamyl-o-methyl-p-(N,N-diethylamiino)anilide obtained in Referential Example 1, there is obtained L-γ-glutamyl-p-(N,N-dipropylaino)anilide or L-γ-glutamyl-o-methyl-p-(N,N-diethylamino)anilide.

EXAMPLE 3

Reagent solutions:

(1) Substrate buffer solution: A buffer solution of 0.05 mole/l. of boric acid of pH 8.0 containing 10 mmole/l. of L-γ-glutamyl-p-(N,N-diethylamino)anilide obtained in Example 1, 20 mmole/l. of glycylglycine, 0.2 mmole/l. of 1-naphthol-2-sulfonic acid and 2% of ethylene glycol is prepared.

(2) Oxidation reagent solution: A buffer soluion of 0.3 mole/l. of boric acid of pH 8.0 containing 0.2% potassium periodate is prepared.

Measuring procedure:

To 1.0 ml of the substrate buffer solution, 0.02 ml of serum sample is added and mixed well. Subsequently the mixture is warmed at 37° C. in a constant temperature bath for 15 minutes. To the mixture, 2.0 ml of the oxidation reagent solution is added to color develop. Absorbance of the sample at 670 nm is measured. As a control, a reagent blank test solution is also prepared in the same manner as mentioned above except for using 0.02 ml of water in place of the serum sample and its absorbance is also measured. γ-GTP activity is calculated by comparing with the calibration curve which has been prepared according to a conventional method using N,N-diethyl-p-phenylenediamine.

EXAMPLE 4

Reagent solutions:

(1) Substrate buffer solution: A buffer solution of 0.05 mole/l. of boric acid of pH 8.0 containing 10 mmole/l. of L-γ-glutamyl-p-(N,N-dimethylamino)anilide obtained in Example 2 and 20 mmole/l. of glycylglycine is prepared. (2) Oxidation reagent solution: A buffer solution of 0.3 mole/l. of boric acid of pH 8.0 containing 0.2% potassium periodate is prepared.'

Measuring procedure:

To 2.0 ml of the substrate buffer solution, 0.02 ml of serum sample is added and mixed well. Subsequently the mixture is warmed at 37° C. in a constant temperature bath for 15 minutes. To the mixture, 2.0 ml of the oxidation reagent solution is added to color develop. Absorbance of the sample at 510 nm is measured. As a control, a reagent blank test solution is also prepared in the same manner as mentioned above except for using 0.02 ml of water in place of the serum sample and its absorbance is also measured. γ-GTP activity is calculated by comparing with the calibration curve which has been prepared according to a conventional method using p-(N,N-dimethylamino)aniline.

EXAMPLE 5

Using L-γ-glutamyl-p-(N,N-dipropylamino)anilide obtained in Example 2 as a substrate, γ-GTP activity is calculated in the same manner as described in Example 3.

EXAMPLE 6

Using L-γ-glutamyl-o-methyl-p-(N,N-diethylamino)anilide obtained in Example 2 as a substrate, γ-GTP activity is calculated in the same manner as described in Example 3.

What is claimed is:

1. A method for measuring γ-glutamyl transpeptidase activity in a living sample which comprises using as a substrate the γ-glutamyl-p-aminoanilide derivative of the formula:

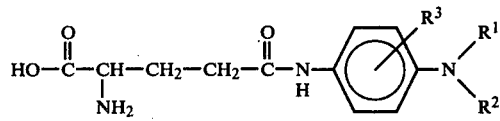

wherein $R^1$ and $R^2$ are independently a lower alkyl group; and $R^3$ is hydrogen, a lower alkyl group, a carboxyl group, or a sulfo group, and determining colorimetrically the amount of p-phenylenediamine derivative liberated by the action of γ-glutamyl transpeptidase.

2. A method according to claim 1, wherein the colorimetrical determination is carried out by color developing the p-phenylenediamine derivative by using an oxidizer.

3. A method according to claim 1, wherein the colorimetical determination is carried out by color developing the p-phenylenediamine derivative by using an oxidizer in the presence of a coupler.

4. A method according to claim 2 or 3, wherein the oxidizer is one member selected from the group consisting of periodates, chloramine T, hydrochlorites, and persulfates.

5. A method according to claim 4, wherein the oxidizer is potassium periodate.

6. A method according to claim 3, wherein the coupler is one member selected from the group consisting of phenol, α-naphthol, β-naphthol, monosulfonic acid derivatives of α or β-naphthol, disulfonic acid derivatives of α or β-naphthol, carboxylic acid derivatives of α or β-naphthol and polyhydric phenols.

7. A method according to claim 6, wherein the coupler is 1-naphthol-2-sulfonic acid.

* * * * *